United States Patent [19]

Rosini et al.

[11] Patent Number: 5,608,084

[45] Date of Patent: Mar. 4, 1997

[54] LACTONES WITH ANTIOXIDISING AND HYPOLIPIDAEMIC ACTIVITY USEFUL IN THE THERAPY OF THE ATHEROSCLEROSIS

[75] Inventors: Goffredo Rosini; Claudia Baldazzi, both of Bologna; Eleonora Romagnoli, Medicina; Stefano Saguatti; Silvano Piani, both of Bologna, all of Italy

[73] Assignee: Alfa Wassermann S.p.A., Alanno Scalo, Italy

[21] Appl. No.: 556,648

[22] Filed: Nov. 13, 1995

[30] Foreign Application Priority Data

Dec. 21, 1994 [IT] Italy ................... BO94A0562

[51] Int. Cl.$^6$ .................... C07D 321/00; C07C 59/90
[52] U.S. Cl. .................... 549/267; 562/464; 562/471; 560/254
[58] Field of Search ................. 549/267; 560/464, 560/471

[56] References Cited

U.S. PATENT DOCUMENTS 5,196,447  3/1993  Pettit et al. .................... 514/450

Primary Examiner—Amelia Owens
Attorney, Agent, or Firm—Bucknam and Archer

[57] ABSTRACT

Lactones of formula

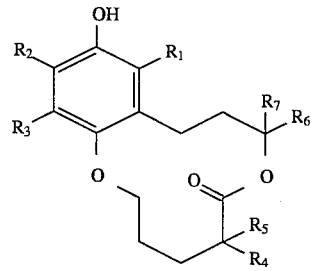

and their pharmacologically acceptable salts endowed with antioxiding and hypolipidaemic properties and that show the capability to prevent and/or to delay the oxidative modification of the lipoproteins by competing with the chain of propagation of the lipidic peroxidation by means of an effective scavenging of the peroxylic radicals. The compounds object of the present invention are useful in the treatment of the atherosclerosis and of many correlated vascular pathologies, like ischaemic cardiopathies (angina pectoris and myocardial infarction), cerebral thrombosis and peripheral arteriopathies, because the high plasma levels of lipids and the oxidative modifications of the low density lipoproteins (LDL) represent crucial events in the pathogenesis of the atherosclerosis.

20 Claims, 2 Drawing Sheets

Latency period (min.)
(negative control-ethanol)

Latency period (min.)
(reference compound-probucol 10µM)

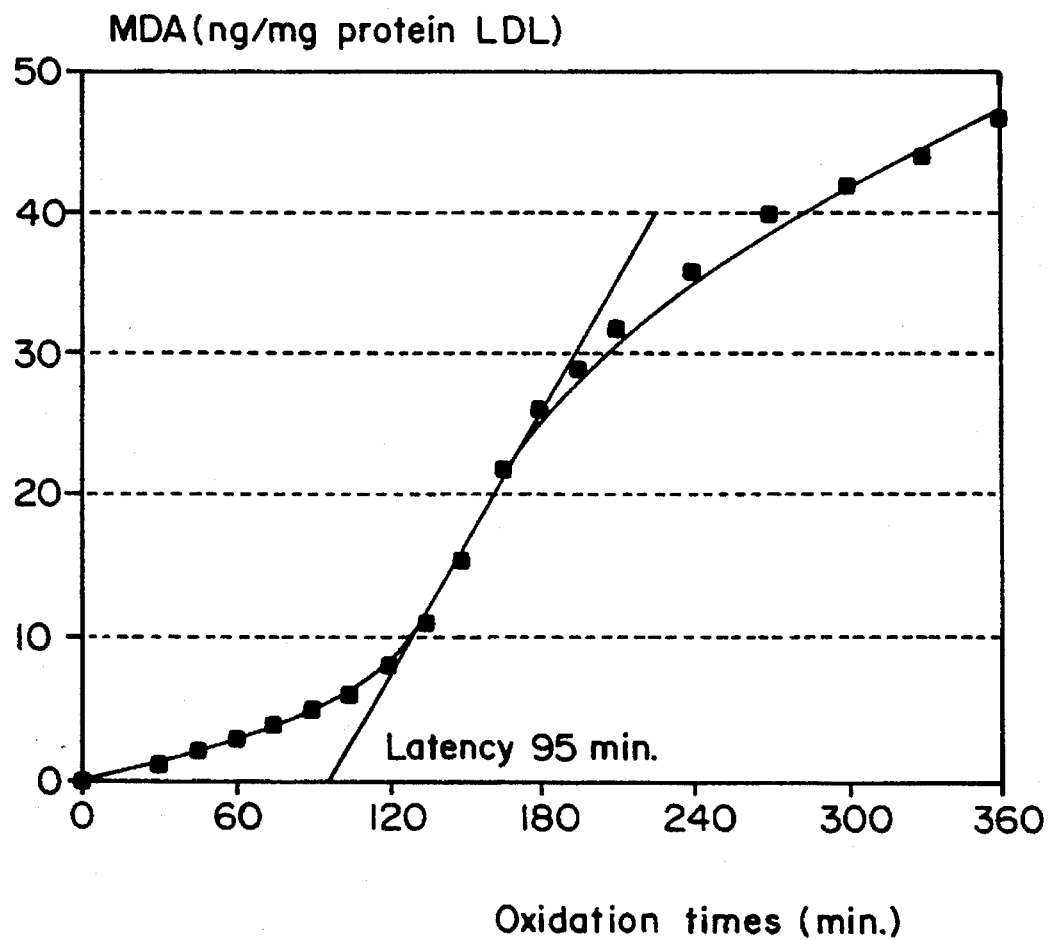

100-4084

LACTONES WITH ANTIOXIDISING AND HYPOLIPIDAEMIC ACTIVITY USEFUL IN THE THERAPY OF THE ATHEROSCLEROSIS

BACKGROUND OF THE INVENTION

The atherosclerosis is a process of degeneration of the arterial wall and represents the main cause of many vascular pathologies like ischaemic cardiopathies (angina pectoris and myocardial infarction) and cerebral thrombosis, main causes of death in the industrial countries.

Many efforts have been carried out to understand the aetiology of this pathology of wide diffusion and importance and to find out the possible therapeutical treatments.

The atherosclerosis is a process with composite aetiology that involves in varied measure different factors and cell types. Ross R. in New Engl. J. Med., 314, 488–495, (1986) assumes that the endothelial damages, caused by exposure to many risk factors, represent the main event in the genesis of the atheroma and in Amer. J. Pathol., 143, 987–1001, (1993) finds out an important cause of the induction of such endothelial damage and of the progress and complication of the atheromatous plaque in the high serum rates of lipids and cholesterol that characterize the hyperlipidaemias and that often aggravate the diabetic pathologies. The pharmacological interventions aimed at lowering the plasma levels of cholesterol and low density lipoproteins (LDL) have proved to be effective in the prevention of the vascular coronary pathologies and in the treatment of atheromatous plaques, as reported by Steinberg D. in J.A.M.A., 253, 2080–2086, (1985) and in Atherosclerosis, 3, 283–301, (1983). The atherogenic risk joined to the LDL appears bound together with not only their plasma concentration but also their qualitative characteristics; the possible modifications of the structure and composition of the LDL in the plasma or in the arterial wall can in fact make these macromolecules more atherogenic, namely more apt to trigger off and to stimulate the formation of the atheromatous plaque, as reported by Steinberg D. in New Engl. J. Med., 320, 915–924, (1989). The oxidative processes that occur by action of oxidizing agents present in the plasma or in the endothelial cells of the arterial wall are of main importance among the modifications that the LDL can undergo in vivo. Many in vitro and in vivo experiments, together with the results of epidemiological investigations, support the hypothesis that this mechanism represent a key event in the development of the atherosclerosis, as reported by Esterbauer H. et al. in Brit. Med. Bull., 49, 566–576, (1993).

In fact Steinberg D. in New Engl. J. Med., 320, 915–924, (1989) shows the presence of antibodies anti-OX-LDL and of OX-LDL, oxidized low density lipoproteins, in the atheromatous lesions of patients suffering from advanced atherosclerosis. Moreover Witzum J. L. and Steinberg D. in J. Clin. Invest., 88, 1785–1792, (1991) report that the OX-LDL are toxic towards the endothelial cells and show a pro-inflammatory activity towards monocytes and lymphocytes and an increased susceptibility to the taking from the macrophages and the smooth muscle cells with formation of foam cells. Such properties can have an important part in the processes of formation and progression of the atheromatous lesion, as reported by Ross R. in Nature, 362, 801–809, (1993).

The LDL are particles not only rich of cholesterol but also of fatty polyunsaturated acids, abbreviation PUFA, highly susceptible to the peroxidation from which they are protected by the presence of many endogenous antioxidizers like tocopherols, carotenes, lycopene and ubiquinol-10.

The oxidation of the LDL is a chain reaction of lipidic peroxidation led by free radicals able to quickly transform the PUFA into lipidic hydroperoxides (propagation period).

The endogenous antioxidizers challenge the chain of propagation by means of an effective scavenging of the peroxylic radicals and the concentration of hydroperoxides increases only when the endogenous antioxidizers are depleted (latency period).

The reactive species of oxygen that form during the process of oxidation together with monounsaturated aldehydes that stem from the decomposition of the hydroperoxides, mainly malondialdehyde (MDA) and 4-hydroxynonenal, cause important changes in the primary structure of the main LDL apoprotein, the B-100 apolipoprotein (apo B-100). Such modification, by helping the LDL absorption by the macrophages, causes the intracellular accumulation of esters of the cholesterol and the formation of foam cells with subsequent development of the atherosclerotic plaque, as reported by Vanderyse L., et al. in Atherosclerosis, 97, 187–199, (1992).

Steinberg D. et al. in Proc. Nat. Acad. Sci. USA, 84, 7725–7729, (1987) show how compounds with antioxidizing action towards the LDL can have a part as anti-atherosclerotic drugs. The effectiveness of a treatment by means of substances having antioxidizing action is based on observations limited to in vitro and animal models and on the in vivo use of the Vitamin E. In fact the atherogenic potentialities of the LDL are remarkably lowered in vitro when the LDL are incubated in presence of antioxidizers, like for instance probucol or Vitamin E, as reported by Esterbaur H. et al. in Amer. J. Clin. Nutr., 53, 314S–321S, (1991).

Studies carried out on Watanabe rabbits, suffering from familial hypercholesterolaemia and with high levels of LDL, showed that the treatment with probucol lowers the atheromatous lesions even if it does not substantially modify the LDL plasma levels, as reported by Kita T. et al. in Proc. Nat. Acad. Sci. USA, 84, 5928–5931, (1987).

Prospective studies on a large scale show a relation between the taking of considerable amounts of Vitamin E and the lowering of the risk of vascular pathologies, both in men and in women, as reported by Rimm E. B. et al. in New Engl. J. Med., 328, 1450–1456, (1993) and by Stampfer M. J. et al. in New Engl. J. Med., 328, 1444–1449, (1993). At present the therapy of the disorders of the lipidic metabolism, like the familiar heterozygotic hypercholesterolaemia, the combined familiar hyperlipidaemia, the dis-β-lipoproteinaemia, the familiar hypertriglyceridaemia and the polygenic hypercholesterolaemia, that are important causes of the atherosclerosis, is based on the use of drugs having hypolipidaemic activity like the fibrates (for instance Gemfibrozil), the acid, the resins sequestering the bile acids and the inhibitors of the enzyme HMGCoA reductase. The metabolic effect of these drugs is that of lowering the plasma concentration of cholesterol (LDL) and partly of the triglycerides (VLDL-LDL) through two mechanisms: an increase of the mediated receptor-removal of the LDL, or a lowering of the synthesis of the VLDL-LDL. Generally the best reductions of the plasma LDL have been obtained by means of the resins sequestering the bile acids and with the statins, inhibitors of the HMGCoA reductase, while the plasma levels of the triglycerides are mostly affected by the treatment with nicotinic acid and fibrates, as reported by Betteridge D. J. in Current Opinion in Lipidology, 4, 49–55, (1993). Therefore, on the basis of the above mentioned considerations, it is reasonable to suppose that molecules having both hypolipidemic and antioxidant activity represent a therapeutic development important in the treatment of the disorders of the lipoproteic metabolism and in the prevention of the atherosclerosis.

The compounds object of the present invention are endowed with antioxidant and hypolipidaemic properties, in particular they show the capability to prevent and/or to delay the oxidative modification of the LDL, i.e. they compete with the chain of propagation of the lipidic peroxidation through an effective scavenging of the peroxylic radicals.

The oxidative modifications of the low density lipoproteins (LDL) represent, as it has already been seen, a key event in the pathogenesis of the atherosclerosis and therefore the compounds object of the present invention can find useful therapeutical application in the treatment of the atherosclerosis and in the prevention of many vascular pathologies like ischaemic cardiopathies (angina pectoris and myocardial infarction), cerebral thrombosis and peripheral arteriopathies.

DESCRIPTION OF THE INVENTION

The present invention resides in lactones of formula

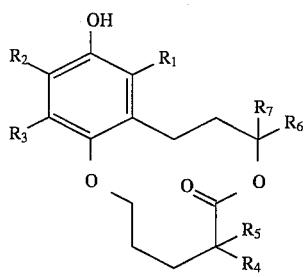

I and to their pharmacologically acceptable salts useful in the therapy of the atherosclerotic pathologies and of the correlated vascular pathologies, like ischaemic cardiopathies, cerebral thrombosis and periferal arteriopathies.

Compounds of formula II and III

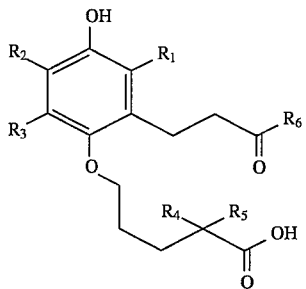

II

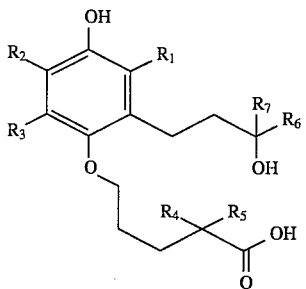

III used in the synthesis of the lactones of formula I are a further object of the invention.

In the compounds of formulae I, II and III $R_1$, $R_2$, $R_3$ and $R_6$ represent a $C_1$–$C_3$-alkyl group and $R_4$, $R_5$ and $R_7$, independently, represent a hydrogen atom or a $C_1$–$C_3$-alkyl group. The preferred compounds are those in which $R_1$, $R_2$ and $R_3$ is a methyl group, $R_4$, $R_5$ and $R_7$, independently, represent a hydrogen atom or a methyl group and $R_6$ represent a methyl or ethyl group. The lactones of formula I and the corresponding intermediates of formulae II and III are obtained through the process reported in the following scheme 1.

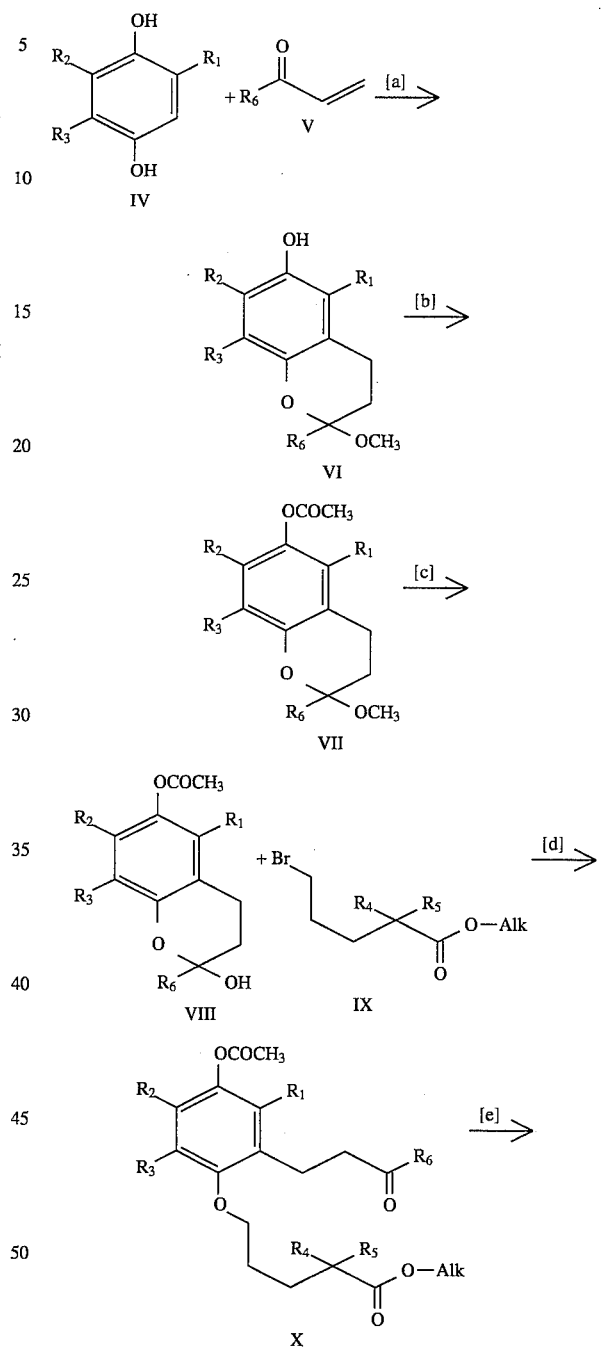

Scheme 1

-continued
Scheme 1

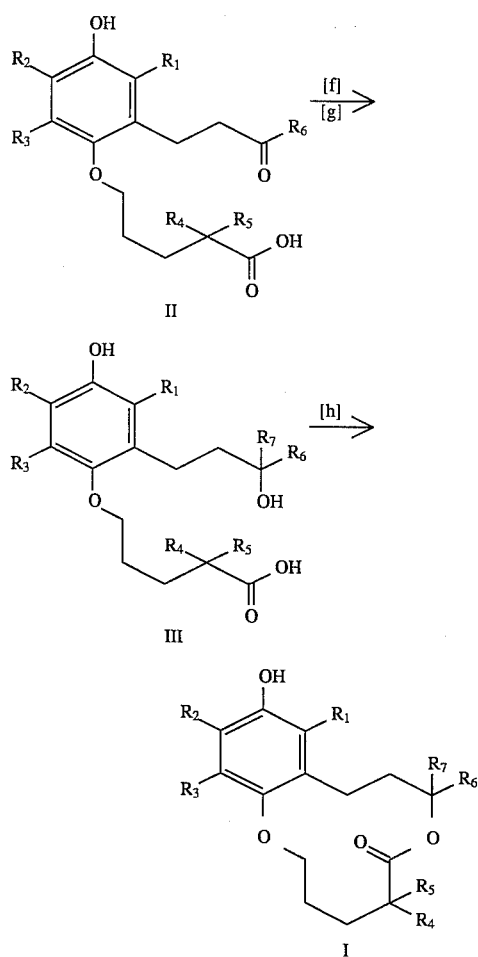

The 3,4-dihydro-2H-1-benzopyrans of formula VI are obtained by reacting, in an alcohol containing from 1 to 3 carbon atoms, in an atmosphere of inert gas and at a temperature comprised between −5° C. and 0° C., from 2 to 3 molar equivalents of an alkylvinylketone of formula V with one molar equivalent of a hydroquinone of formula IV in presence of from 1.2 to 1.4 molar equivalents of trimethylorthoformate and of catalytic amounts of concentrated sulfuric acid and by continuing the reaction, at room temperature, for a period of time between 16 and 24 hours. The products of formula VI are obtained by evaporation of the solvent and possible subsequent crystallization from a solvent or organic solvents' mixture from alcohols, ethers and hydrocarbons. The esters of formula VII, which can be purified by chromatography on silica gel and crystallized in double layer at low temperature, are obtained by treatment of one molar equivalent of the products of formula VI with from 4 to 6 molar equivalents of acetic anhydride in a basic organic solvent, like pyridine, at a temperature comprised between 20° C. and 30° C. and for a period of time between 1 and 24 hours. The selective deprotection of the hydroxyl in position 2 of the pyran ring of the esters of formula VII is obtained by adding concentrated hydrochloric acid in an acetone/water mixture in a ratio between 1:1 and 5:1, preferably 1.25:1, for a period of time between 2 and 8 hours and at a temperature between 40° C. and 60° C. The compounds of formula VIII are recovered by crystallization from mixtures of organic solvents, preferably acetone/water, at low temperature. The products of formula X are obtained by reaction of one molar equivalent of a product of formula VIII with from 1 to 2 molar equivalents of sodium hydride and from 1 to 2 molar equivalents of an alkyl 5-bromopentanoate of formula IX, in an atmosphere of inert gas and in a solvent made by a mixture of an aromatic hydrocarbon, preferably benzene or toluene, with a polar solvent, preferably dimethylsulphoxide, at a temperature between 60° C. and 70° C. for a period of time between 2 and 24 hours. The products are purified and recovered by chromatography on silica gel. The products of formula X are subjected to alkaline hydrolysis with an inorganic base selected from potassium and sodium hydroxide, in an alcohol containing from 1 to 3 carbon atoms, at a temperature between 20° C. and the boiling temperature of the reaction mixture for a period of time between 2 and 24 hours, obtaining the compounds of formula II. The compounds of formula III, where $R_7$ represents a hydrogen atom, are obtained by reduction of the compounds of formula II with from 2 to 5 molar equivalents of sodium borohydride in an alcohol containing from 1 to 3 carbon atoms, at a temperature between 25° C. and 50° C. for a period of time between 10 minutes and 6 hours. The products are recovered by extraction with a suitable organic solvent and by evaporation, or by subsequent crystallization from mixtures of linear chain or cyclic hydrocarbons and organic chlorinated solvents. When $R_7$ represents a $C_1$-$C_3$-alkyl group, the compounds of formula III are synthesized by reaction of the compounds of formula II with a Grignard reagent, at a temperature between 20° C. and the boiling temperature of the reaction mixture, in an anhydrous ethereal solvent, preferably anhydrous ethyl ether, for a time between 1 and 3 hours. After acidifying by means of an aqueous solution of hydrochloric acid the ethereal solution is separated, the crude product is isolated by evaporating the solvent and is purified by filtration on silica gel with suitable mixtures of organic solvents. The lactones of formula I are obtained by cyclization of the compounds of formula III that initially are reacted in an organic solvent, preferably acetonitrile, with from 2 to 2.2 molar equivalents of 2,2'-dipyridyldisulfide and from 2 to 2.2 molar equivalents of triphenylphosphine and then with from 2 to 3 molar equivalents of silver perchlorate hydrate in an aromatic hydrocarbon, preferably p-xylene. After a period of time between 12 and 24 hours, at a temperature between 25° C. and the boiling temperature of the reaction mixture, the lactones of formula I are recovered by evaporation of the solvent and by chromatographic filtration on silica gel with suitable solvents and purified, if necessary, by subsequent crystallization. The pharmacologically acceptable salts of the lactones of formula I are obtained by cold mixing equimolar amounts, or in slight excess (1.1–1.2 equivalents) of the suitable base dissolved in a solvent selected from alcohols containing from 1 to 6 carbon atoms, cyclic or acyclic ethers and mixtures thereof with the lactones of formula I, dissolved in mixtures of the same solvents at a temperature between 0° C. and the room temperature and by filtering the precipitated salt.

Salts of organic compounds, like aminoacids, in particular alanine, lysine, arginine, asparagine and glycine, and trometanol, are preferred in the realization of the present invention.

The determination of the melting point has been carried out by means of a capillary melting point apparatus Electrothermal, without any correction. The I.R. spectrum has been obtained by means of a Perkin-Elmer rood. 963/G spectrophotometer generally, when not otherwise specified, preparing the specimen in potassium bromide and recording the spectrum between 4000 and 600 nm. The $^1$H-NMR spectrum has been recorded at room temperature with a 200 MHz Varian Gemini spectrometer, in the solvents cited, by using tetramethylsilane as internal standard; the resonances of the signals have been expressed in p.p.m.. The $^{13}$C-NMR spectrum has been carried out at 50.3 MHz with a Varian Gemini 200 spectrometer by using tetramethylsilane as internal standard and as solvents those described in the experimental section. The mass spectrum has been recorded by using a VG 7070E mass spectrometer, at a 70 eV ionization voltage and with a 6 Kvolt acceleration voltage. The chromatographies on silica gel have been carried out by using 60 F254 silica gel (230–240 mesh—Merck) with the eluents cited in the examples, according to the method described by Clark Still W. et al. in J. Org. Chem., 43, 2923, (1978). The pharmacological activity of the lactones of formula I object of the present invention has been determined by means of a series of in vitro tests considered predictive of the antioxidant and hypolipidaemic properties. The antioxidant activity has been evaluated through the capability of some lactones of formula I to prevent and/or delay the oxidative modification of the lipoproteins (LDL), caused by a chemical method by incubating native LDL with cupric ions, according to the method described by Steinbrecher U. P. in J. Biol. Chem., 262, 3603–3608, (1987). The evaluation of the oxidation degree of the LDL through the monitoring of the concentration of aldehydes derived from the degradation of the lipidic peroxides and the observation of the modifications of the B-100 apolipoprotein represent the used experimental approach. The antioxidant activity of the lactones has been expressed in terms of duration of the latency period that represents a parameter of the resistance to the oxidation of the LDL. The LDL have been isolated from the human plasma obtained from blood collected, in the presence of EDTA, from healty volunteers fasting from 8 hours according to the method described by Havel H. in J. Clin. Invest., 34, 1345–1353, (1955). The solution, dialyzed in Visking-Serva dialysis tubes at 4° C. for 72 hours in phosphate buffer (PBS) added with EDTA (0.24 mM), has been filtered through a membrane with 0.45µ porosity (Millex HV Filters) and the proteic concentration has been determined according to the method described by Lowry O. et al. in J. Biol. Chem., 193, 265–275, (1951). The solution has been diluted with PBS-EDTA at a concentration of 500 µg protein/ml and the obtained LDL have been incubated at 42° C. for 45 minutes in presence of the lactones solubilized in ethanol (1.7 µl/ml LDL). At the end of the incubation the solutions have been placed on ice for 45 minutes and dialyzed at 4° C. for 36 hours in PBS. The oxidation of the LDL has been carried out with 5 µM cupric sulfate at 37° C. and stopped at the experimental times by cooling at 4° C. and adding 0.24 mM of EDTA. The solutions of LDL have been kept at 4° C. and sheltered from light during the experimental procedure. The oxidation degree of the LDL has been checked by spectrophotometric determination ($\lambda$=535 nm—Perkin Elmer spectrophotometer mod. Lambda 1) of the content of the aldehydes of degradation reactive to the thiobarbituric acid using as standard malondialdehyde (MDA), according to the TBARS method, described in Methods in Enzymology, vol. 52, (1978).

BRIEF DESCRIPTION OF THE DRAWINGS

FIGS. 1A–1C show the results of spectrophotometric readings expressed as ng of MDA/mg LDL protein.

Figure 1A:
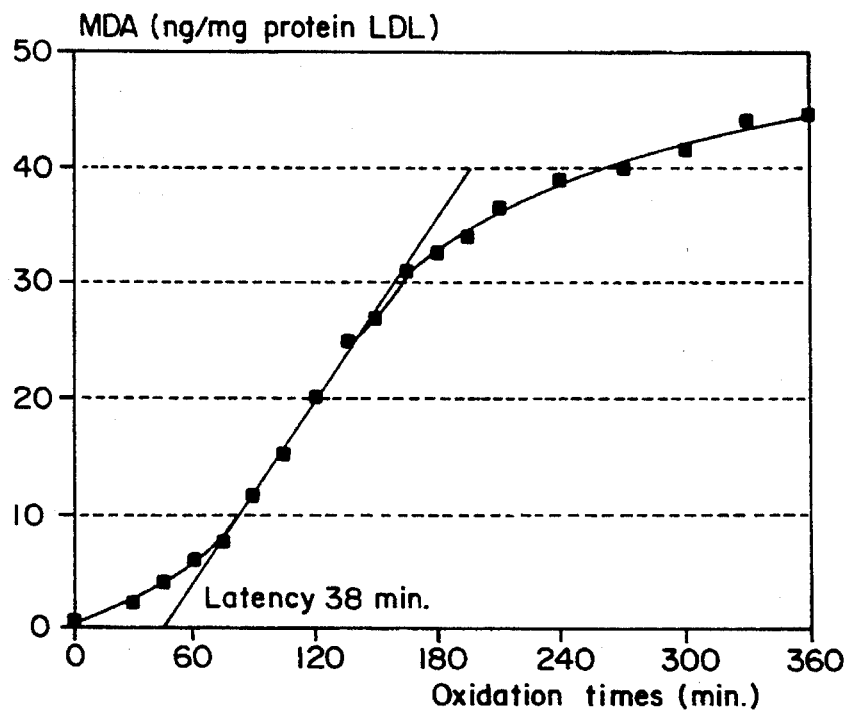
Figure 1B:
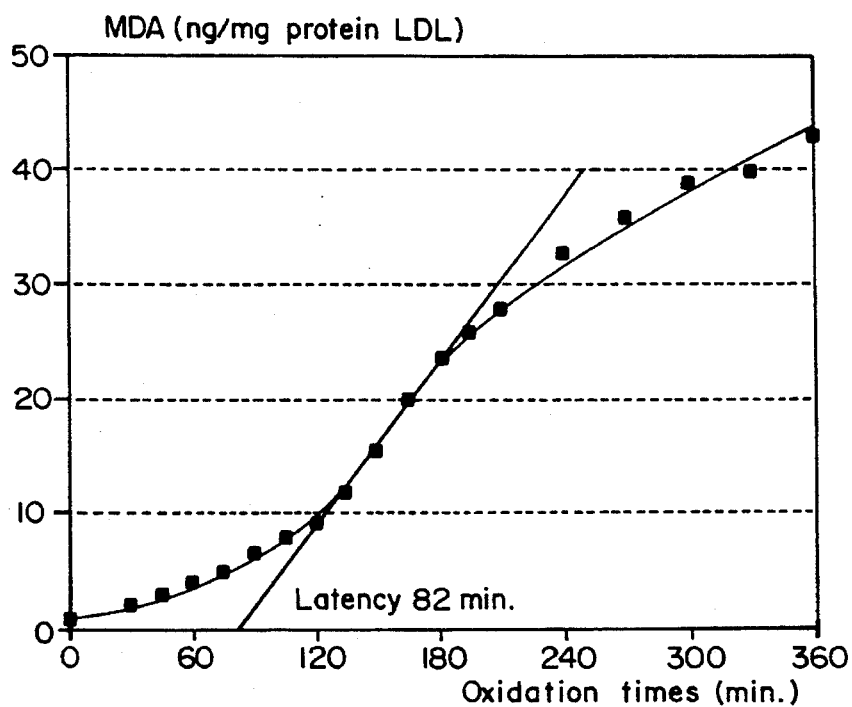

The results of the spectrophotometric readings, expressed as ng of MDA/mg LDL protein, have been reported in function of the oxidation time, obtaining a graphic having a sigmoidal development (FIGS. 1a–c). The latency interval has been determined as the intercept on the axis of abscissas of the tangent to the curve in the flex point. The results referred to the lactones described in examples 3 and 6 of the present invention are reported in Table 1 and it is very interesting to notice how they show an antioxidant activity far higher than that of probucol; as a matter of fact a comparable prolongation of the latency period is observed at a concentration 10 times lower than that of probucol.

TABLE 1

| | Latency period | | |
|---|---|---|---|
| | Latency periods (minutes) | | |
| Compound | 1 µM | 5 µM | 10 µM |
| Probucol | — | — | 82 |
| Lactone (Example 3) | 73 | 120 | >180 |
| Lactone (Example 6) | 95 | >180 | >180 |

The inhibition of the oxidative process has also been qualitatively studied through the evaluation of the modification of the surface-negative charge of the B-100 apolipoprotein by electrophoretic analysis on agarose gel, by using the method described in the kit "Titan gel Multi-slot lipo-17 electrophoresis system" (Cat. no. 3095), manufactured by Helena Laboratories.

The Bio-Phoresis Horizontal Electrophoresis Cell Bio-Rad (Cat. no. 1702900) has been used as electrophoretic cell. The modification of the surface-negative charge of the B-100 apolipoprotein, caused by the oxidation of the LDL, produces an increase of the anionic electrophoretic mobility. Therefore the evaluation of the varying of this electrophoretic datum, mobility in presence of antioxidant substances, represents an indirect measure of the antioxidant capabilities of the claimed compounds as reported by Vanderyse L. et al. in Atherosclerosis, 97, 187–199, (1992). The evaluation has been carried out at the times 0, 60, 90, 120, 150, 180, 360 minutes in order to maximize the differences between the compounds and the controls. The migration of the native LDL is taken as a reference equal to 0 (no electrophoretic migration), while the migration of the band of the copper-oxidized LDL at the time of 360 minutes, only in presence of ethanol, is taken as reference equal to 100. The data of relative electrophoretic mobility (REM), expressed as percent variation, at the times 180 and 360 minutes, with reference to the lactones of examples 3 and 6 and to probucol, at the 10 µM concentration, by using ethanol as control, are reported in table 2. The data show that the lactones, by preventing the oxidative modifications of the LDL, lower their electrophoretic mobility in a manner remarkably more effective than probucol.

TABLE 2

| | Electrophoretic activity on agarose gel | |
|---|---|---|
| Compound | REM (%) at 180' | REM (%) at 360' |
| Ethanol | 60 | 100 |
| Probucol | 40 | 100 |
| Example 3 | 15 | 30 |
| Example 6 | 15 | 30 |

The inhibition of the oxidative process has been evaluated also by means of the study of the fragmentation of the B-100 apolipoprotein through the electrophoretic analysis on polyacrylamide gel in presence of sodium dodecylsulfate (SDS-PAGE), according to the method described by Laemmli U. K., in Nature, 227, 680, (1970). The quantitative evaluation of the disappearance of the B-100 apolipoprotein has been carried out by densitometric unidimensional measurement of the absorbance at $\lambda$=633 nm, on an electrophoretic plate 13.5 cm long, after colouring with Coomassie Brillant Blue. The reagents used for the preparation and coloration of the gels, the reference standard (SDS-PAGE standards Broad Range—Cat. no. 161-0317), the gradient former (gradient former Bio-Rad Mod. 385) and the electrophoretic cell (Protean II) are Bio-Rad products; the feeder is a LKB Pharmacia Mod. 2197, the densitometer is a Pharmacia LKB Mod. 2222-020 Ultrascan XL with integrators LKB 2220 and LKB 2190 GelScan Software Package. The oxidative modifications of the LDL go with a degradation of the B-100 apolipoprotein in an heterogeneous mixture of fragments having a lower molecular weight; therefore the evaluation of such a degradation represents a predictive indication of the antioxidant effectiveness of the claimed compounds as reported by Fong L. G. et al. in J. Lipid Res., 28, 1466–1477, (1987). The densitometric values related to the areas of the peaks of the B-100 apolipoprotein, expressed as absorbance units per millimeter, for the lactones of examples 3 and 6 and for the probucol, as reference, all used at the concentration of 10 μM, are reported in Table 3.

TABLE 3

Oxidative modifications on SDS-PAGE

Area (AU/mm)

| Compound | 0 minutes | 60 minutes | 90 minutes | 120 minutes | 150 minutes | 180 minutes | 360 minutes |
|---|---|---|---|---|---|---|---|
| Ethanol | 2.3 | 1.7 | 1.5 | 0.5 | 0.4 | 0.3 | 0.2 |
| Probucol | 2.7 | 1.8 | 1.6 | 0.9 | 0.9 | 0.6 | 0.3 |
| Example 3 | 2.2 | 2.0 | 1.9 | 1.6 | 1.5 | 1.5 | 1.5 |
| Example 6 | 2.5 | 2.3 | 2.1 | 2.0 | 1.7 | 1.6 | 1.6 |

The data show how the claimed compounds prevent the disappearance of the B-100 apolipoprotein in a more efficient manner in respect of the probucol, as it can be taken from the almost constant maintenance of the area of the peaks of the B-100 apolipoprotein at the envisaged times.

The hypolipidaemic activity of some lactones of general formula I has been evaluated in vitro by testing their influence on the synthesis of the cell lipids like cholesterol, fatty acids, triglycerides, phospholipids and esters of the cholesterol, described by Barnhard J. W. in Amer. J. Cardiol., 62, 52B–56B, (1988).

The synthesis of the lipids has been studied by incubating cells coming from a human hepatocarcinoma (HepG2- American Type Culture Collection) in presence of $^{14}C$-acetate (Amersham) and by measuring the incorporation of the radioactive precursor in the main lipidic classes by means of chromatographic separation on silica gel (Merck F254), according to the method described by Skipski V. P. et al. in Biochem. Biophys. Acta, 106, 386–396, (1965) and by means of scintillographic dosage with β-counter Beckman scintillator, according to the method reported by Gherardi E. and Calandra S. in Lipids, 15, 108–112, (1980).

The data reported in tables 4 and 5 refer to the incorporation of $^{14}C$-acetate in the various lipidic classes, expressed as radioactivity in count per minute (cpm) for culture plate, for some lactones, in comparison with the probucol and the gemfibrozil, used as positive controls and with the solvent ethanol, used as negative control.

TABLE 4

Incorporation of $^{14}C$-acetate in the lipidic classes

| Compound | | Cholesterol (cpm) | Esters of Cholesterol (cpm) |
|---|---|---|---|
| Physiological solution | | 31613 | 4066 |
| Ethanol | | 26517 (−16%) | 1467 (−64%) |
| Probucol | 1 μM | 14360 (−55%) | 1887 (−54%) |
| | 10 μM | 11389 (−64%) | 2635 (−35%) |
| Gemfibrozil | 1 μM | 20820 (−34%) | 968 (−76%) |
| | 10 μM | 25306 (−20%) | 1156 (−71%) |
| Example 3 | 1 μM | 23364 (−26%) | 1347 (−67%) |
| | 10 μM | 19034 (−40%) | 1107 (−73%) |
| Example 6 | 1 μM | 23597 (−25%) | 1098 (−73%) |
| | 10 μM | 17458 (−45%) | 1148 (−72%) |

The data show how the lactones of examples 3 and 6 interfere with the synthesis of cholesterol in manner comparable to that of gemfibrozil and lower than that of the probucol. However the two lactones show an activity greater (60–75%) than that of the probucol (about 35–45%) and completely comparable to that of gemfibrozil (70–75%) as regards the synthesis of the esters of the cholesterol. The data referred to the other lipidic classes emphasize how the two lactones practically show the same influence on the synthesis of the fatty acids and of the phospholipids in comparison both with the probucol and the gemfibrozil whereas the influence on the synthesis of the triglycerides, on which only the gemfibrozil shows a remarkable activity, is practically absent.

TABLE 5

| | Incorporation of $^{14}$C-acetate in the lipidic classes | | |
|---|---|---|---|
| Compound | | Triglycerides (cpm) | Fatty acids (cpm) | Phospholipids (cpm) |
| Physiological solution | | 108549 | 670 | 249863 |
| Ethanol | | 116544 (+7%) | 468 (−30%) | 190843 (−24%) |
| Probucol | 1 µM | 100202 (−8%) | 429 (−36%) | 173426 (−31%) |
| | 10 µM | 105097 (−3%) | 394 (−42%) | 173329 (−31%) |
| Gemfibrozil | 1 µM | 84593 (−22%) | 299 (−55%) | 132598 (−47%) |
| | 10 µM | 96533 (−11%) | 376 (−44%) | 164252 (−34%) |
| Example 3 | 1 µM | 109681 (−1%) | 473 (−29%) | 181053 (−27%) |
| | 10 µM | 104271 (−4%) | 368 (−45%) | 195274 (−22%) |
| Example 6 | 1 µM | 107497 (−1%) | 386 (−42%) | 160997 (−35%) |
| | 10 µM | 110154 (+1%) | 332 (−50%) | 177323 (−29%) |

The percents in brackets express the lowering of the $^{14}$C-acetate in the various lipidic classes referred to the control, i.e. to the physiological solution. The toxicity of the lactones described in examples 3 and 6 has been evaluated in vitro by means of the cytotoxic effect on HepG2 cells, according to the method reported by Cingi R. et al. in Toxicol. in vitro, 5, 119–125, (1991). The confluence cells have been exposed to the products tested for 24 hours; at the end of the incubation the monolayer has been solubilized and the optical density of the lysate at λ260 nm has been measured. The value of the absorbance is direct function of the amount of the macromolecules present and therefore indirectly of the number of the cells. In table 6 are reported the values of $LD_{50}$, expression of the concentration of the claimed compounds, in solution both of ethanol and of dimethylsulfoxide, able to cause a 50% lowering of the total macromolecules.

TABLE 6

| | In vitro toxicity on HepG2 cells($DL_{50}$) | |
|---|---|---|
| Compound | Dimethylsulfoxide | Ethanol |
| Probucol | — | >$10^{-3}$ |
| Gemfibrozil | >$10^{-4}$ | — |
| Example 3 | $2.5 \cdot 10^{-5} \div 5 \cdot 10^{-5}$ | $2.5 \cdot 10^{-5} \div 5 \cdot 10^{-5}$ |
| Example 6 | $5 \cdot 10^{-5} \div 7.5 \cdot 10^{-5}$ | >$10^{-4}$ |

The data prove how the two lactones checked in this test show a cytotoxicity far lower than those of probucol and gemfibrozil.

The examples hereinafter reported have to be considered as an illustration of the present invention and not as an its limitation.

EXAMPLE 1

2,2-Dimethyl-5-[4-hydroxy-2-(3-oxobutyl)-3,5 6-trimethylphenoxy]pentanoic acid a) 5-[4-Acetoxy-2-(3-oxobutyl)-3,5,6-trimethylphenoxy]-2,2-dimethylpentanoic acid, isopropyl ester A solution containing 14.0 g (0.053 moles) of 6-acetoxy-3,4-dihydro-2-hydroxy-2,5,7,8-tetramethyl-2H-1-benzopyran in 240 ml of benzene is added, by slow dripping and under nitrogen atmosphere, to a suspension containing 1.82 g (0.074 moles) of 97% sodium hydride in 100 ml of dimethylsulfoxide. After 40 minutes the solution is dripped into a solution containing 13.3 g (0.052 moles) of 2,2-dimethyl-5-bromopentanoic acid isopropyl ester in 60 ml of benzene and the mixture is reacted at 65° C. for 19 hours. The reaction mixture is then diluted with ethyl ether and water, acidified to pH 5 by means of a 10% aqueous solution of hydrochloric acid and the product is recovered pure by chromatography on silica gel column with eluent ethylene chloride-ethyl ether in 90:10 ratio. After evaporating the solvent an oil is obtained, 13.03 g with a yield of 58%, having the following chemical-physical characteristics:

$^1$H-NMR (CDCl$_3$) δ(ppm): 1.20 (6H, s, geminal CH$_3$); 1.23 (6H, d, J=6.2 Hz, 2 isopropyl CH$_3$); 1.71 (4H, m, —CH$_2$CH$_2$C); 2.02 (3H, s, arom. CH$_3$); 2.04 (3H, s, arom. CH$_3$); 2.15 (3H, s, CH$_3$—CO—); 2.16 (3H, s, arom. CH$_3$); 2.34 (3H, s, CH$_3$COO); 2.54–2.68 (2H, m, —CH$_2$—); 2.78–2.90 (2H, m, —CH$_2$—); 3.60–3.70 (2H, m, CH$_2$O); 5.00 (1H, m, J=6.2 Hz, isopropyl CH).

$^{13}$C-NMR (CDCl$_3$) δ(ppm): 12.6 (arom. CH$_3$); 13.1 (arom. CH$_3$); 13.2 (arom. CH$_3$); 10.6 (CH$_3$COO—); 21.7 (—COCH$_3$); 21.9 (OCH(CH$_3$)$_2$); 25.2 ((CH$_3$)$_2$COO); 26.1 (CH$_2$); 29.9 (CH$_2$); 37.1 (CH$_2$); 42.1 (CH$_2$COO—); 44.0 (CH$_2$CH$_2$CO); 67.6 (isopropyl CH); 73.8 (OCH$_2$); 126.8; 128.2; 128.7; 131.3; 144.9; 153.9 (arom. 6 C); 169.6 (CH$_3$COO—); 177.7 (CCOO—); 208.6 (—CO—). IR (film) ν(cm$^{-1}$); 1757, 1719 (C=O). MS (m/z): 434 (M$^+$), 222, 171, 129, 43.

b) 2,2-Dimethyl-5-[4-hydroxy-2-(3-oxobutyl)-3,5,6-trimethylphenoxy]pentanoic acid A solution containing 12.8 g (0.029 moles) of 5-[4-acetoxy-2-(3-oxobutyl)-3,5,6-trimethylphenoxy]-2,2-dimethyl pentanoic acid isopropyl ester in 90 ml of 95% ethanol is added with 90 ml of 95% ethanol containing 14.9 g (0.264 moles) of potassium hydroxide. The reaction mixture is kept at 90° C. for 22 hours and then is diluted by addition of ethyl ether and water, acidified to pH 5 with a 10% aqueous solution of hydrochloric acid and the product is extracted with ethyl ether. The crude product obtained by evaporation of the solvent is purified by chromatography on silica gel column with the eluent methylene chloride-ethyl ether 60:40. 5.58 grams of product with a yield of 55% are obtained showing the following chemical-physical characteristics:

m.p.=106°–108° C.

$^1$H-NMR (CDCl$_3$) δ(ppm): 1.25 (6H, s, 2 geminal CH$_3$); 1.72–1.88 (4H, m, CH$_2$CH$_2$C); 2.0 (3H, s, arom. CH$_3$); 2.18 (9H, s, 2 arom. CH$_3$ and CH$_3$CO); 2.56–2.70 (2H, m, CH$_2$); 2.80–3.00 (2H, m, CH$_2$); 3.60–3.70 (2H, m, CH$_2$O) IR (KBr) ν(cm$^{-1}$): 3363 (OH), 1737 (C=O), 1702 (C=O). MS (m/z): 350 (M$^+$); 222; 164; 43.

EXAMPLE 2

2,2-Dimethyl-5-[4-hydroxy-2-(3-hydroxybutyl)-3,5,6-trimethylphenoxy]pentanoic acid A solution containing 4.2 g (0.012 moles) of 2,2-dimethyl-5-[4-hydroxy-2-(3-oxobutyl)-3,5,6-trimethylphenoxy]pentanoic acid in 125 ml of methanol is added with 4.9 g (0.129 moles) of sodium borohydride. After 4 hours at room temperature the reaction mixture is added with ethyl ether and with a 6M aqueous solution of hydrochloric acid and the product is recovered by evaporating the ethyl ether. 3.92 grams of product are obtained, with a yield of 93%, showing the following chemical-physical characteristics:

m.p.=44°–46° C.

$^1$H-NMR (CDCl$_3$)δ(ppm): 1.15 (3H, d, J=6.8 Hz, CH$_3$CH); 1.30 (6H, s, geminal CH$_3$); 1.50–1.90 (6H, m, 3 CH$_2$); 2.10 (3H, s, arom. CH$_3$); 2.18 (6H, s, 2 arom. CH$_3$); 2.65–2.88 (2H, m, CH$_2$); 3.52–3.72 (3H, m, CH$_2$OH); 5.48 (2H, broad s, 2 OH). IR (KBr) ν(cm$^{-1}$): 3213 (OH), 1702 (C=O). MS (m/z): 352 (M$^+$), 224, 206, 164.

EXAMPLE 3

6,6,9,13,15,16-Hexamethyl-14-hydroxy-2,8-dioxabicyclo[10.4.0]hexadec-12,14,16-trien-7-one 2.0 Grams (0.005 moles) of 5-[4-hydroxy-2-(3-hydroxybutyl-3,5,6-trimethylphenoxy]-2,2-dimethylpentanoic acid are reacted, under nitrogen atmosphere, with 2.5 g (0.011 moles) of 2,2'-dipyridyldisulfide dissolved in 60 ml of anhydrous acetonitrile and with 3.0 g (0.011 moles) of triphenyl phosphine and the resulting mixture is kept for 4 hours at 25° C. The reaction mixture is then diluted with 70 ml of p-xylene and added, by slow dripping, to a solution containing 2.74 g (0.012 moles) of silver perchlorate hydrate in 150 ml of p-xylene previously heated to reflux. The reaction mixture is boiled for 18 hours and then the crude product is recovered by evaporating the solvent and is purified by chromatography on silica gel column by using as eluent petroleum ether-ethyl ether 50:50. The pure product, 0.77 g with a yield of 46%, shows the following chemical-physical characteristics:

m.p.=127°–130° C.

$^1$H-NMR (CDCl$_3$) δ(ppm): 1.18 (3H, s, CH$_3$C); 1.22 (3H, d, J=6.4 Hz, CH$_3$CH); 1.27 (3H, s, CH$_3$C); 1.50–1.90 (5H, m, 2 CH$_2$ and CH$_2$); 2.12 (3H, s, arom. CH$_3$); 2.14 (3H, s, arom. CH$_3$); 2.16 (3H, s, arom. CH$_3$); 2.35 (1H, m, CH$_2$); 2.55 (1H, m, CH$_2$); 3.05 (1H, m, CH$_2$); 3.65 (2H, m, CH$_2$O); 4.50 (1H, s, OH); 4.85 (1H, m, CHO).

$^{13}$C-NMR (CDCl$_3$) δ(ppm): 12.3 (arom. CH$_3$); 12.6 (arom. CH$_3$); 13.6 (arom. CH$_3$); 19.2 (CH$_3$CH); 21.8 (CH$_2$); 23.5 (CH$_3$C); 26.1 (CH$_2$); 28.6 (CH$_2$); 36.0 (CH$_2$); 38.1 (CH$_2$); 42.7 (C); 69.6 (CH); 73.1 (CH$_2$); 120.0; 121.2; 128.1; 131.5; 148.5; 150.2 (6 arom. C); 177.9 (COO) IR (KBr) ν(cm$^{-1}$); 3452 (OH), 1709 (C=O). MS (m/z): 334 (M$^+$), 206, 164, 119, 91.

EXAMPLE 4

2,2-Dimethyl-5-[4-hydroxy-2-(3-oxopentyl)-3,5,6-trimethylphenoxy]pentanoic acid a) 3,4-Dihydro-2-ethyl-6-hydroxy-2-methoxy-5,7,8-trimethyl-2H-1-benzopyran A solution containing 30.0 g (0.198 moles) of trimethylhydroquinone in 150 ml of methanol is added with 30 ml (0.274 moles) of trimethylorthoformate, cooled to 0° C. under nitrogen atmosphere and added with 0.6 ml of concentrated sulfuric acid. 39 Ml (0.396 moles) of ethylvinylketone are dripped into the solution in 60 minutes while keeping constant the temperature. The reaction mixture is kept at room temperature for 20 hours and the raw product is recovered by evaporation of the solvent under reduced pressure and is purified by chromatography on silica gel column with eluent petroleum ether-ethyl ether 70:30. By subsequent crystallization in double layer from ethyl ether and n-hexane 39.6 g of pure product are obtained, with a yield of 80%, showing the following chemical-physical characteristics:

m.p.=97°–99° C.

$^1$H-NMR (CDCl$_3$) δ(ppm): 1.0 (3H, t, J=7.3 Hz, —CCH$_2$CH$_3$); 1.57–2.10 (4H, m, 2 CH$_2$); 2.13 (3H, s, arom. CH$_3$); 2.18 (6H, s, 2 arom. CH$_3$); 2.42–2.90 (2H, m, CH$_2$); 3.20 (3H, s, OCH$_3$); 4.27 (1H, s, OH).

$^{13}$C-NMR (CDCl$_3$) δ(ppm): 8.5 (—CCH$_2$CH$_3$); 11.7 (arom. CH$_3$); 12.1 (arom. CH$_3$); 12.65 (arom. CH$_3$); 20.2 (CH$_2$); 28.8 (—(CH$_2$)$_2$—); 48.9 (OCH$_3$); 99.7 (acetalic C); 119.2; 119.3; 121.6; 122.7; 144.4; 145.9 (6 arom. C). IR (KBr) ν(cm$^{-1}$): 3469 (OH). MS (m/z): 250 (M$^+$), 164, 221, 189, 87.

b) 6-Acetoxy-3,4-dihydro-2-ethyl-2-methoxy-5,7,8-trimethyl-2H-1-benzopyran

A solution containing 32.3 g (0.129 moles) of 3,4-dihydro-2-ethyl-6-hydroxy-2-methoxy-5,7,8-trimethyl-2H-1-benzopyran in 37.5 ml (0.465 moles) of pyridine is added by dripping into 61.5 ml (0.720 moles) of acetic anhydride under nitrogen atmoshpere. The mixture is left reacting for one hour at room temperature and the crude product is extracted with methylene chloride. The organic layer is washed by means of a saturated aqueous solution of cupric sulfate and then with water. The product, after evaporation of the solvent, is purified by filtration on chromatographic column of silica gel with eluent petroleum ether-ethyl ether in 70:30 ratio. The pure product is obtained by crystallization in double layer from ethyl ether and n-hexane at −20° C., 32.4 g with a yield of 86% and shows the following chemical-physical characteristics:

m.p.=71°–73° C.

$^1$H-NMR (CDCl$_3$) δ(ppm): 0.95 (3H, t, J=7.4 Hz, —CCH$_2$CH$_3$); 1.60–1.90 (2H, m, CH$_2$); 1.92–2.20 (2H, m, CH$_2$); 1.96 (3H, s, arom. CH$_3$); 2.05 (3H, s, arom. CH$_3$); 2.11 (3H, arom CH$_3$); 2.35 (3H, s, OCOCH$_3$); 2.49–2.87 (2H, m, CH$_2$); 3.18 (3H, s, OCH$_3$).

$^{13}$C-NMR (CDCl$_3$) δ(ppm): 8.1 (—CCH$_2$CH$_3$); 11.7 (arom. CH$_3$); 12.1 (arom. CH$_3$); 13.0 (arom. CH$_3$); 19.1 (CH$_2$); 20.6 (OCOCH$_3$); 28.1 (CH$_2$); 28.4 (CH$_2$); 48.5 (OCH$_3$); 99.6 (acetalic C); 119.2; 122.8; 125.1; 126.8; 141.5; 147.9 (6 arom. C); 169.7 (—OCOCH$_3$). IR (KBr) ν(cm$^{-1}$): 1753 (C=O) MS (m/z): 292 (M$^+$), 260, 250, 217, 189, 164, 43.

c) 6-Acetoxy-3,4-dihydro-2-ethyl-2-hydroxy-5,7,8-trimethyl-2H-1-benzopyran 0.88 Ml of a 37% aqueous solution of hydrochloric acid are dripped into a solution containing 32.0 g (0.109 moles) of 6-acetoxy-3,4-dihydro-2-ethyl-2-methoxy-5,7,8-trimethyl-2H-1-benzopyran in 225 ml of an acetone-water mixture in 5:4 ratio. After having distilled off 120 ml of solvent, the reaction mixture is slowly cooled to 60° C. and 80 ml of acetone are added. The reaction mixture after 4 hours at 55°

C. is extracted three times with methylene chloride, the crude product is obtained by evaporation of the solvent and is purified on chromatography column of silica gel with eluent petroleum ether-ethyl ether in 60:40 ratio. The pure product is obtained by crystallization in double layer from ethyl ether-n-hexane at −20° C., 24.24 g with a yield of 80% and shows the following chemical-physical characteristics:

m.p.=85°–87° C. $^1$H-NMR (CDCl$_3$) δ(ppm): 1.05 (3H, t, J=7.4 Hz, CCH$_2$CH$_3$); 1.70–1.95 (4H, m, 2 CH$_2$); 1.99 (3H, s, arom. CH$_3$); 2.02 (3H, s, arom. CH$_3$); 2.10 (3H, s, arom. CH$_3$); 2.32 (3H, s, COCH$_3$); 2.61 (1H, d, J=1.9 Hz, OH); 2.65–2.86 (2H, m, CH$_2$).

$^{13}$C-NMR (CDCl$_3$) δ(ppm): 8.1 (—CCH$_2$CH$_3$); 12.3 (arom. CH$_3$); 12.5 (arom. CH$_3$); 13.0 (arom. CH$_3$); 20.2 (CH$_2$); 20.95 (COCH$_3$); 29.5 (CH$_2$); 34.6 (CH$_2$); 97.5 (emiacetalic C); 118.6; 123.4; 125.5; 127.4; 140.9; 148.5 (6 arom. C); 170.1 (OCOCH$_3$). IR (KBr) ν(cm$^{-1}$); 3382 (OH), 1729 (C=O). MS (m/z): 278 (M$^+$), 236, 164.

d) 5-[4-Acetoxy-2-(3-oxopentyl)-3,5,6-trimethylphenoxy]-2,2-dimethyl pentanoic acid, isopropyl ester A solution containing 20.0 g (0.072 moles) of 6-acetoxy-3,4-dihydro-2-ethyl-2-hydroxy-5,7,8-trimethyl-2H-1-benzopyran in 500 ml of benzene is slowly dripped, under nitrogen atmosphere, into a suspension containing 2.07 g (0.086 moles) of 97% sodium hydride in 150 ml of dimethylsulfoxide. After 40 minutes the solution is dripped into a solution containing 21.6 g (0.086 moles) of 2,2-dimethyl-5-bromopentanoic acid isopropyl ester in 100 ml of benzene brought to 60° C. and the mixture is reacted for 3 hours at 60° C. Then the suspension is diluted with ethyl ether and water, acidified with a 10% aqueous solution of hydrochloric acid and the product is recovered by evaporation of the organic solvent and purified by chromatography on column of silica gel with eluent petroleum ether-ethyl ether in 60:40 ratio. After evaporation of the solvent, 16.6 g are obtained with a yield of 83% of an oil having the following chemical-physical characteristics:

$^1$H-NMR (CDCl$_3$) δ(ppm); 0.95 (3H, t, J=7.3 Hz, COCH$_2$CH$_3$); 1.12 (6H, s, C(CH$_3$)$_2$); 1.18 (6H, d, J=6.2 Hz, OCH(CH$_3$)$_2$); 1.63 (4H, m, CH$_2$CH$_2$); 1.91 (3H, s, arom. CH$_3$); 1.98 (3H, s, arom. CH$_3$); 2.10 (3H, s, arom. CH$_3$); 2.22 (3H, s, COCH$_3$); 2.35 (2H, q, J=7.4 Hz, COCH$_2$CH$_3$); 2.51 (2H, m, CH$_2$); 2.80 (2H, m, CH$_2$); 3.58 (2H, m, CH$_2$O); 4.90 (1H, m, J=6.5 Hz, OCH(CH$_3$)$_2$).

$^{13}$C-NMR (CDCl$_3$) δ(ppm): 8.5 (COCH$_2$CH$_3$); 13.1 (arom. CH$_3$); 13.6 (arom. CH$_3$); 13.7 (arom. CH$_3$); 21.1 (COCH$_3$); 22.35 (OCH(CH$_3$)$_2$); 25.7 (CH$_3$)$_2$CCO); 26.6 (CH$_2$CH$_2$O); 36.5 (CH$_2$); 37.6 (CH$_2$); 42.5 (C(CH$_3$)$_2$); 43.0 (CH$_2$); 67.9 (CH(CH$_3$)$_2$); 74.1 (OCH$_2$); 126.9; 128.3; 128.8; 131.65; 144.9; 154.0 (6 arom. C); 169.7 (CH$_3$COO); 177.7 (COO); 211.3 (CO). IR (film) ν(cm$^{-1}$): 1758 (C=O), 1716 (C=O). MS (m/z): 448 (M$^+$), 279, 236, 171, 129, 43.

e) 2,2-Dimethyl-5-[4-hydroxy-2-(3-oxopentyl)-3,5,6-trimethylphenoxy]pentanoic acid A solution containing 22.6 g (0.40 moles) of potassium hydroxide in 300 ml of 95% ethanol is added, under nitrogen atmosphere, to a solution containing 20.0 g (0.045 moles) of 5-[4-acetoxy-2-(3-oxopentyl)-3,5,6-trimethylphenoxy)-2,2-dimethyl-pentanoic acid, isopropyl ester in 100 ml of 95% ethanol. The reaction mixture is heated to the boiling for 18 hours and then is diluted by adding ethyl ether and water, acidified to pH 5 with a 10% aqueous solution of hydrochloric acid and the product extracted with ethyl ether. The raw product, obtained by evaporation of the solvent, is purified by filtration on a column of silica gel with eluent ethyl ether. The pure product, 11.1 g with a yield of 65%, obtained by subsequent crystallization from n-hexane, shows the following chemical-physical characteristics:

m.p.=108°–110° C.

$^1$H-NMR (CDCl$_3$) δ(ppm): 1.05 (3H, t, J=7.3 Hz, COCH$_2$CH$_3$); 1.25 (6H, s, C(CH$_3$)$_2$); 1.75 (4H, s, 2 CH$_2$); 2.15 (3H, s, arom. CH$_3$); 2.2 (6H, s, 2 arom. CH$_3$); 2.45 (2H, q, J=7.0 Hz, COCH$_2$CH$_3$); 2.6 (2H, m, CH$_2$); 2.85 (2H, m, CH$_2$); 3.7 (2H, s, OCH$_2$); 4.9 (2H, broad s, 2 OH).

$^{13}$C-NMR (CDCl$_3$) δ(ppm): 8.2 (COCH$_2$CH$_3$); 12.1 (arom. CH$_3$); 12.6 (arom. CH$_3$); 13.3 (arom. CH$_3$); 22.0 (COCH$_2$CH$_3$); 25.2 (C(CH$_3$)$_2$); 26.2 (CH$_2$); 36.2 (CH$_2$); 37.2 (CH$_2$); 42.2 (C(CH$_3$)$_2$); 43.0 (CH$_2$); 73.9 (OCH$_2$); 120.2; 121.6; 128.0; 130.7; 148.6; 149.6 (6 arom. C); 184.3 (COOH); 211.9 (CO). IR (KBr) ν(cm$^{-1}$): 3499 (OH), 1715 (C=O). MS (m/z): 364 (M$^+$), 236, 164, 57.

EXAMPLE 5

2,2-Dimethyl-5-[4-hydroxy-2-(3-hydroxypentyl)-3,5,6-trimethylphenoxy]pentanoic acid A solution containing 8.0 g (0.022 moles) of 2,2-dimethyl-5-[4-hydroxy-2-(3-oxopentyl)-3,5,6-trimethylphenoxy]pentanoic acid in 240 ml of methanol are slowly added with 9.04 g (0.024 moles) of sodium borohydride under nitrogen atmosphere. The reaction mixture after one hour of reaction at room temperature is diluted with 240 ml of ethyl ether, acidified with a 6N aqueous solution of hydrochloric acid and the product is extracted with ethyl ether. The pure product, 8.16 g with a yield of 93%, obtained after evaporation of the solvent, shows the following chemical-physical characteristics:

m.p.=38°–42° C.

$^1$H-NMR (CDCl$_3$) δ(ppm): 0.9 (3H, t, J=8 Hz, CH$_2$CH$_3$); 1.25 (6H, s, C(CH$_3$)$_2$); 1.4–1.65 (m, 4H, CH$_2$CH$_2$); 1.7–1.9 (m, 4H, CHCH$_2$CH$_2$); 2.15 (s, 9H, 3 arom. CH$_3$); 2.7–2.85 (2H, m, CH$_2$CH$_3$); 3.3–3.45 (m, 1H, CH); 3.6–3.75 (m, 2H, OCH$_2$); 6.1–7.0 (bs, 3H, 3 OH).

$^{13}$C-NMR (CDCl$_3$) δ(ppm): 10.4 (CH$_3$); 12.25 (arom. CH$_3$); 12.7 (arom. CH$_3$); 13.5 (arom. CH$_3$); 23.5 (CH$_2$); 25.45 (CH$_3$); 26.3 (CH$_2$); 30.2 (CH$_2$); 37.2 (CH$_2$); 42.35 qC); 72.8 (CH); 74.5 (CH$_2$); 120.5; 121.6; 127.75; 131.3; 149.0; 149.7 (6 arom. C); 183.3 (CO). IR (KBr) ν(cm$^{-1}$): 3499 (OH), 1710 (C=O). MS (m/z): 366 (M$^+$), 348, 322, 238, 220, 165.

EXAMPLE 6

9-Ethyl-14-hydroxy-6,6,13,15,16-pentamethyl-2,8-dioxabicyclo[10.4.0]hexadec-12,14,16-trien-7-one 4.76 Grams (0.022 moles) of 2,2'-dipyridyldisulfide dissolved in 110 ml of anhydrous acetonitrile and 5.66 g (0.022 moles) of triphenylphosphine are added under nitrogen atmosphere to 4.00 g (0.011 moles) of 2,2-dimethyl-5-[4-hydroxy-2-(3-hydroxypentyl)-3,5,6-trimethylphenoxy]pentanoic acid. The reaction mixture after 3 hours at 25° C. is diluted with 120 ml of p-xylene and added during the time of one hour to a boiling solution containing 5.2 g (0.025 moles) of silver perchlorate hydrate in 300 ml of p-xylene. After 12 hours of boiling the raw product is recovered by evaporation of the solvent and purified by chromatography on column of silica gel with eluent ethyl ether-petroleum ether in the ratio 50:50. The pure product obtained by crystallization from ethyl ether and n-hexane, 1.76 g with a yield of 46%, shows the following chemical-physical characteristics:

m.p.=126°–128° C.

¹H-NMR (CDCl₃) δ(ppm): 0.9 (t, J=8 Hz, 3H, CH₂CH₃); 1.2 (s, 3H, CH₃); 1.3 (s, 3H, CH₃); 1.4–1.9 (m, 7H, CH₂CH₃, CH₂CH₂ 1H CH₂CH₂CH); 2.15 (s, 9H, 3 arom. CH₃); 2.35–2.6 (m, 2H, CH₂CH); 2.9–3.1 (m, 1H, 1H CH₂CH₂CH); 3.5–3.8 (m, 2H, CH₂); 4.55 (s, 1H, OH); 4.75–4.9 (m, 1H, CH).

¹³C-NMR (CDCl₃) δ(ppm): 10.4 (CH₃); 12.3 (arom. CH₃); 12.7 (arom. CH₃); 13.7 (arom. CH₃); 21.5 (CH₂); 23.5 (CH₃); 26.6 (2 CH₂); 28.6 (CH₃); 33.7 (CH₂); 37.3 (CH₂); 42.7 (qC); 72.8 (CH₂); 74.9 (CH); 120.0; 121.2; 128.1; 131.9; 148.4; 150.3 (6 arom. C); 178.2 (CO). IR (KBr), ν(cm⁻¹): 3448 (OH); 1699 (C=O). MS (m/z): 348 (M⁺), 220, 165.

EXAMPLE 7

5-[4-Hydroxy-2-(3-oxobutyl)-3,5,6-trimethylphenoxy]-pentanoic acid a) 5-[4-Acetoxy-2-(3-oxobutyl)-3,5,6-trimethylphenoxy]pentanoic acid, ethyl ester A solution containing 15.0 g (0.057 moles) of 6-acetoxy-3,4-dihydro-2-hydroxy-2,5,7,8-tetramethyl-2H-1-benzopyran in 270 ml of benzene and 45 ml of dimethylsulfoxide is slowly dripped, under nitrogen atmosphere, into a suspension containing 1.98 g (0.080 moles) of 97% sodium hydride in 110 ml of dimethylsulfoxide. The reaction mixture, after 40 minutes, is slowly dripped into a solution containing 13.1 g (0.062 moles) of ethyl 5-bromovalerate in 80 ml of benzene and the mixture is reacted at 65° C. for 21 hours. The suspension is diluted with ethyl ether and water and acidified by means of a 10% aqueous solution of hydrochloric acid. The organic layer is filtered on a layer of silica 4 cm high and the product is recovered pure after elimination of the solvent and of the excess of reagents at the temperature of 170° C. and at the pressure of 2.0 millibar. The pure product under form of a thick oil, 16.76 g with yield of 75%, presents the following chemical-physical characteristics:

¹H-NMR (CDCl₃) δ(ppm): 1.3 (t, J=7.5 Hz, 3H, OCH₂CH₃); 1.75–1.9 (m, 4H, CH₂CH₂); 2.1 (s, 6H, 2 arom. CH₃); 2.15 (s, 6H, 1 arom. CH₃ and COCH₃); 2.3–2.5 (m, 2H, CH₂COOEt); 2.35 (s, 3H, OCOCH₃); 2.55–2.7 (m, 2H, CH₂CH₂COCH₃); 2.75–2.9 (m, 2H, CH₂CH₂COCH₃); 3.6–3.8 (m, 2H, OCH₂CH₂); 4.15 (q, J=7.5 Hz, 2H, OCH₂CH₃)

¹³C-NMR (CDCl₃) δ(ppm): 10.4 (CH₃); 12.3 (arom. CH₃); 12.7 (arom. CH₃); 13.7 (arom. CH₃); 21.5 (CH₂); 23.5 (CH₃); 26.6 (2 CH₂); 28.6 (CH₃); 33.7 (CH₂); 37.3 (CH₂); 42.7 (qC); 72.8 (CH₂); 74.9 (CH); 120.0; 121.2; 128.1; 131.9; 148.4; 150.3 (6 arom. C); 178.2 (CO). IR (film), ν(cm⁻¹): 1750, 1730, 1710 (3 C=O). MS (m/z): 392 (M⁺), 347, 277, 265, 129, 101.

b) 5-[4-Hydroxy-2-(3-oxobutyl)-3,5,6-trimethylphenoxy]pentanoic acid

A solution containing 10.0 g (0.026 moles) of 5-[4-acetoxy-2-(3-oxobutyl)-3,5,6-trimethylphenoxy]pentanoic acid, ethyl ester in 60 ml of 96% ethanol cooled to 0° C. is added, by slow dripping, with 170 ml of 96% ethanol containing 7.1 g (0.127 moles) of potassium hydroxide. After 3 hours at 25° C. the solution is diluted with ethyl ether and water, acidified to pH 5 by means of a 10% aqueous solution of hydrochloric acid and, after separating the layers, the crude product is recovered by evaporation of the solvent. The pure product, 5.82 g with a yield of 67%, obtained by crystallization in double layer from methylene chloride and n-hexane, shows the following chemical-physical characteristics:

m.p.=104°–106° C.

¹H-NMR (CDCl₃) δ(ppm): 1.75–1.95 (m, 4H, CH₂CH₂); 2.2–2.25 (m, 12H, 3 arom. CH₃ and COCH₃); 2.4–2.55 (m, 2H, CH₂COOH); 2.55–2.7 (m, 2H, CH₂CH₂COCH₃); 2.80–2.95 (m, 2H, CH₂CH₂COCH₃); 3.6–3.75 (m, 2H, OCH₂CH₂)

¹³C-NMR (CDCl₃) δ(ppm): 12.2 (arom. CH₃); 12.65 (arom. CH₃); 13.4 (arom. CH₃); 22.0 (2CH₂); 30.15 (CH₂ and COCH₃); 34.2 (CH₂); 44.55 (CH₂); 73.4 (CH₂); 120.2; 121.55; 128.2; 130.8; 148.7; 149.8 (6 arom. C); 178.85 (COOH); 209.1 (COCH₃). IR (KBr), ν(cm⁻¹): 3478 (OH), 1709 (2 C=O) MS (m/z): 322 (M⁺), 304, 222, 164.

EXAMPLE 8

5-[4-Hydroxy-2-(3-hydroxybutyl)-3,5,6-trimethylphenoxy]pentanoic acid

A solution containing 5.0 g (0.016 moles) of 5-[4-hydroxy-2-(3-oxobutyl)-3,5,6-trimethylphenoxy]pentanoic acid in 150 ml of methanol is added with 5.90 g (0.156 moles) of sodium borohydride at a temperature lower than 50° C. After 30 minutes at room temperature the reaction mixture is added with ethyl ether and with a 10% aqueous solution of hydrochloric acid and, after separation of the organic layer, the crude product is recovered by evaporation of the solvent. The product is purified by filtration on a 3 cm high layer of silica by eluting with a 95:5 mixture of ethyl ether-petroleum ether and by means of a subsequent crystallization from a solution of chloroform and n-hexane. 4.25 Grams, with a yield of 82%, of product are obtained, having the following chemical-physical characteristics:

m.p.=91°–94° C.

¹H-NMR (CDCl₃) ppm: 1.15 (d, J=6.5 Hz, 3H, CH₃); 1.5–1.7 (m, 2H, CHCH₂); 1.75–1.95 (m, 4H, CH₂CH₂); 2.15 (s, 9H, 3 arom. CH₃); 2.35–2.50 (m, 2H, CH₂COOH); 2.6–2.9 (m, 2H, CH₂CH₂CH); 3.5–3.8 (m, 3H, OCH₂ and CH); 6.1 (bs, 3H, 3 OH).

¹³C-NMR (CDCl₃) ppm: 12.3 (arom. CH₃); 12.7 (arom. CH₃); 13.5 (arom. CH₃); 22.0 (CH₂); 23.0 (CH₃); 23.5 (CH₂); 30.0 (CH₂); 34.2 (CH₂); 39.2 (CH₂); 66.9 (CH); 74.0 (CH₂); 120.5; 121.6; 127.8; 130.9; 149.1; 149.4 (6 arom. C); 178.0 (COOH). IR (KBr), ν(cm⁻¹): 3400 (OH), 1709 (C=O) MS (m/z): 324 (M⁺), 224, 206, 165.

EXAMPLE 9

4-Hydroxy-9,13,15,16-tetramethyl-2,8-dioxabicyclo[10.4.0]hexadec-12,14,16-trien-7-one A solution containing 3.0 g (0.009 moles) of 5-[4-hydroxy-2-(3-hydroxybutyl)-3,5,6-trimethylphenoxy]pentanoic acid in 100 ml of anhydrous acetonitrile is added, under nitrogen atmosphere, with 4.1 g (0.019 moles) of 2,2'-dipyridyldisulfide and to 4.9 g (0.019 moles) of triphenylphosphine. After 4 hours at 25° C. the reaction mixture is diluted with 120 ml of anhydrous p-xylene and slowly dripped into a solution containing 4.4 g (0.021 moles) of silver perchlorate hydrate in 420 ml of boiling p-xylene. After 18 hours the crude product is recovered by distillation of the solvents and purified by filtration on a 4 cm high packed layer of silica by eluting with a mixture of methylene chloride-ethyl ether in 90:10 ratio. The pure product, 1.29 g with a yield of 47%, obtained by crystallization from n-hexane, shows the following chemical-physical characteristics:

m.p.=173°–175° C.

¹H-NMR (CDCl₃) δ(ppm): 1.23 (d, J=6.5 Hz, 3H, CH₃); 1.6–2.05 (m, 6H, CH₂CH and CH₂CH₂); 2.05–2.32 (m, 1H, 1H CH₂CH₂CH); 2.15 (s, 9H, 3 arom. CH₃); 2.45–2.65 (m, 2H, CH₂CO); 2.98–3.15 (m, 1H, 1H CH₂CH₂CH); 3.58–3.70 (m, 2H, OCH₂); 4.57 (s, 1H, OH); 4.72–4.87 (m, 1H, CH)

¹³C-NMR (CDCl₃) δ(ppm): 12.3 (arom. CH₃); 12.7 (arom. CH₃); 13.4 (arom. CH₃); 20.1 (CH₃); 21.5 (CH₂); 23.0 (CH₂); 30.7 (CH₂); 35.8 (CH₂); 37.9 (CH₂); 69.6 (CH); 72.6 (CH₂); 120.1; 121.29; 128.3; 131.5; 146.7; 149.6 (6 arom. C); 174.2 (CO). IR (KBr), ν(cm⁻¹): 3395 (OH); 1690 (C=O). MS (m/z): 306 (M⁺), 206, 164.

EXAMPLE 10

5-[4-Hydroxy-2-(3-oxopentyl)-3,5,6-trimethylphenoxy]pentanoic acid a) 5-[4-Acetoxy-2-(3-oxopentyl)-3,5,6-trimethylphenoxy]pentanoic acid, ethyl ester A solution containing 10.0 g (0.036 moles) of 6-acetoxy-3,4-dihydro-2-ethyl-2-hydroxy-5,7,8-trimethyl-2H-1-benzopyran in 100 ml of benzene and 30 ml of dimethylsulfoxide is rapidly dripped, under nitrogen atmosphere, into a suspension containing 1.0 g (0.040 moles) of 97% sodium hydride in 50 ml of dimethylsulfoxide. The solution, after 60 minutes, is cooled to 5° C. and added, by slow dripping, to 50 ml of benzene containing 8.3 g (0.040 moles) of ethyl 5-bromovalerate, while keeping a temperature lower than 25° C. After 24 hours the reaction mixture is diluted with ethyl ether and water, acidified with a 10% aqueous solution of hydrochloric acid and the crude product is recovered by evaporating the organic layer. The pure product, 9.06 g with a yield of 62%, obtained in form of a thick oil by chromatography on a column of silica gel with eluent methylene chloride-ethyl ether in 96:4 ratio, shows the following chemical-physical characteristics:

¹H-NMR (CDCl₃) δ(ppm): 1.1 (t, J=7.5 Hz, 3H, CH₂CH₃); 1.25 (t, J=7.5 Hz, 3H, OCH₂CH₃); 1.75–1.9 (m, 4H, CH₂CH₂); 2.1 (s, 6H, 2 arom. CH₃); 2.15 (s, 3H, 1 arom. CH₃); 2.3–2.5 (m, 7H, CH₂CH₃, COCH₃, CH₂COOEt); 2.5–2.75 (m, 2H, CH₂CH₂COEt); 2.75–2.9 (m, 2H, CH₂CH₂COEt); 3.6–3.75 (m, 2H, OCH₂CH₂); 4.15 (q, J=7.5 Hz, 2H, OCH₂CH₃).

¹³C-NMR (CDCl₃) δ(ppm): 8.3 (CH₃); 12.9 (arom. CH₃); 13.4 (arom. CH₃); 13.5 (arom. CH₃); 14.7 (CH₃); 20.9 (CH₃); 22.1 (2 CH₂); 30.2 (CH₂); 34.5 (CH₂); 36.3 (CH₂); 42.8 (CH₂); 60.7 (CH₂); 73.3 (CH₂); 126.8; 128.2; 126.7; 131.5; 144.8; 153.8 (6 arom. C); 169.6 (COOCH₃); 173.8 (COOEt); 211.3 (COEt). IR (film), ν(cm⁻¹): 1775, 1770, 1734 (3 C=O) MS (m/z): 406 (M⁺), 361, 236, 219.

b) 5-[4-Hydroxy-2-(3-oxopentyl)-3,5,6-trimethylphenoxy]pentanoic acid

A solution containing 8.0 g (0.020 moles) of 5-[4-acetoxy-2-(3-oxopentyl)-3,5,6-trimethylphenoxy]pentanoic acid, ethyl ester in 50 ml of 96% ethanol is cooled to 0° C. and added, by slow dripping and under nitrogen atmosphere, with 70 ml of 96% ethanol containing 5.5 g (0.098 moles) of potassium hydroxide. After 3 hours at 25° C. the solution is diluted by adding ethyl ether and water, acidified to pH 5 with a 10% aqueous solution of hydrochloric acid and the crude product, after separation of the organic phase, is recovered by evaporating the solvent. The pure product, 4.77 g with a yield of 71%, obtained by crystallization from ethyl ether and n-hexane, shows the following chemical-physical characteristics:

m.p.=92°–93° C.

¹H-NMR δ(ppm): 1.1 (t, J=7.5 Hz, 3H, CH₂CH₃); 1.75–1.9 (m, 4H, CH₂CH₂); 2.15 (s, 9H, 3 arom. CH₃); 2.35–2.5 (m, 4H, CH₂CH₃ and CH₂COOH); 2.5–2.65 (m, 2H, CH₂CH₂COEt); 2.8–2.95 (m, 2H, CH₂CH₂COEt); 3.6–3.75 (m, 2H, OCH₂CH₂); 5.0–7.0 (bs, 2H, 2 OH).

¹³C-NMR δ(ppm): 12.3 (arom. CH₃); 12.8 (arom. CH₃); 13.4 (arom. CH₃); 22.0 (CH₂); 22.1 (CH₂); 30.1 (CH₂); 34.3 (CH₂); 36.4 (CH₂); 43.2 (CH₂); 73.4 (CH₂); 120.4; 121.7; 128.1; 130.9; 148.8; 149.6 (6 arom. C); 169.6 (COOH); 212.3 (COEt). IR (KBr), ν(cm⁻¹): 3419 (OH), 1709 (2 C=O). MS (m/z): 336 (M⁺), 236, 164, 57.

EXAMPLE 11

5-[4-Hydroxy-2-(3-hydroxypentyl)-3,5,6-trimethylphenoxy]pentanoic acid

A solution containing 4.1 g (0.012 moles) of 5-[4-hydroxy-2-(3-oxopentyl)-3,5,6-trimethylphenoxy]pentanoic acid in 120 ml of methanol is slowly added, under nitrogen atmosphere, with 4.6 g (0.121 moles) of sodium borohydride; the reaction is immediate and the temperature rises until 50° C. At the end of the addition, 70 ml of ethyl ether and a 10% aqueous solution of hydrochloric acid are added to the reaction mixture; the crude product, after separation of the organic layer, is recovered by evaporation of the solvent. The pure product, 3.85 g with a 95% yield, obtained by further elimination of the organic solvent by cold evaporation under vacuum shows the following chemical-physical characteristics:

m.p.=96°–99° C.

¹H-NMR (CDCl₃) δ(ppm): 0.9 (t, J=7.5 Hz, 3H, CH₂CH₃); 1.35–1.5 (m, 2H, CH₂CH₃); 1.5–1.7 (m, 2H, CH₂CH); 1.75–1.95 (m, 4H, CH₂CH₂): 2.15 (s, 9H, 3 arom. CH₃); 2.35–2.5 (m, 2H, CH₂COOH); 2.6–2.85 (m, 2H, CH₂CH₂CH); 3.25–3.4 (m, 1H, CH); 3.6–3.7 (m, 2H, OCH₂); 6.3 (bs, 3H, 3 OH).

¹³C-NMR (CDCl₃) δ(ppm): 12.3 (arom. CH₂); 12.8 (arom. CH₃); 13.5 (arom. CH₃); 21.9 (CH₂); 23.4 (CH₂); 30.0 (CH₂); 30.1 (CH₂); 34.3 (CH₂); 37.0 (CH₂); 72.4 (CH); 73.9 (CH₂); 120.5; 121.6; 127.8; 131.0; 149.1; 149.5 (6 arom. C); 178.7 (COOH). IR (KBr), ν(cm⁻¹): 3408 (OH), 3216 (OH), 1709 (C=O). MS (m/z): 338 (M⁺), 238, 220, 165.

EXAMPLE 12

9-Ethyl-14-hydroxy-13,15,16-trimethyl-2,8-dioxabicyclo[10.4.0]hexadec-12,14,16-trien-7-one 4.0 Grams (0.016 moles) of 2,2'-dipyridyldisulfide and 4.7 g (0.016 moles) of triphenylphosphine are added, under nitrogen atmosphere, to a solution containing 3.0 g (0.009 moles) of 5-[4-hydroxy-2-(3-hydroxypentyl)-3,5,6-trimethylphenoxy]pentanoic acid in 90 ml of anhydrous acetonitrile. After 4 hours at 25° C. the reaction mixture is diluted with 100 ml of anhydrous p-xylene and slowly dripped into a boiling solution containing 4.26 g (0.020 moles) of silver perchlorate hydrate in 400 ml of p-xylene. After boiling for 17 hours, the crude product is recovered by evaporation of the solvent and is purified by quick filtration on a 4 cm high packed layer of silica gel with eluent methylene chloride-ethyl ether in 90:10 ratio. The pure product obtained by crystallization from ethyl ether-n-hexane, 1.84 g with a yield of 64%, shows the following chemical-physical characteristics:

m.p.=145°–146° C.

$^1$H-NMR (CDCl$_3$) δ(ppm): 0.9 (t, J=7.5 Hz, 3H, CH$_2$CH$_3$); 1.5–2.35 (m, 9H); 2.1 (s, 3H, arom. CH$_3$); 2.12 (s, 3H, arom. CH$_3$); 2.18 (s, 3H, arom. CH$_3$); 2.35–2.7 (m, 2H, CH$_2$CO); 2.95–3.15 (m, 1H); 3.5–3.7 (m, 2H, OCH$_2$); 4.7–4.9 (m, 2H, CH and OH).

$^{13}$C-NMR (CDCl$_3$) δ(ppm): 10.1 (CH$_3$); 12.1 (arom. CH$_3$); 12.4 (arom. CH$_3$); 13.2 (arom. CH$_3$); 21.2 (CH$_2$); 22.2 (CH$_2$); 26.7 (CH$_2$); 30.9 (CH$_2$); 33.6 (CH$_2$); 37.1 (CH$_2$); 71.9 (CH); 75.1 (CH$_2$); 76.7 (CH$_2$); 120.3; 121.4; 128.1; 131.9; 148.6; 149.8 (6 arom. C); 164.1 (CO). IR (KBr), ν(cm$^{-1}$): 3433 (OH); 1700 (C=O). MS (m/z): 320 (M$^+$), 291, 220, 165.

EXAMPLE 13

2,2-Dimethyl-5-[4-hydroxy-2-(3-hydroxy-3-methyl-pentyl)-3,5,6-trimethylphenoxy]pentanoic acid Under nitrogen atmosphere, 4.7 g (0.192 moles) of magnesium are completely soaked in anhydrous ethyl ether, then a solution containing 12 ml (0.019 moles) of methyl iodide in 60 ml of anhydrous ethyl ether is added by slow dripping and the reaction mixture reaches the boiling temperature by exothermy. At the end of the exothermic reaction the mixture, kept to the boiling, is added, by slow dripping, to a solution containing 10.0 g (0.027 moles) of 2,2-dimethyl-5-[4-hydroxy-2-(3-oxopentyl)-3,5,6-trimethylphenoxy]pentanoic acid in 600 ml of anhydrous ethyl ether. After two hours the reaction mixture is cooled, acidified with a 10% aqueous solution of hydrochloric acid, the ethereal solution is separated and the crude product, recovered by evaporation of the solvent, is purified by filtration on silica gel with eluent ethyl acetate-methylene chloride in 10:1 ratio. The pure product, 5.13 g with a yield of 50%, obtained by crystallization from a mixture of ethyl ether-n-hexane, shows the following chemical-physical characteristics:

m.p.=128°–130° C.

$^1$H-NMR (CDCl$_3$ δ(ppm): 0.9 (t, J=7.5 Hz, 3H, CH$_2$CH$_3$); 1.3 (s, 9H, C(CH$_3$)$_2$ and CH$_3$COH); 1.5–1.65 (m, 4H, CCH$_2$CH$_2$ and CH$_2$CH$_3$), 1.75–1.85 (m, 4H, CH$_2$CH$_2$CH$_2$C); 2.2 (s, 9H, 3 arom. CH$_3$); 2.6–2.75 (m, 2H, CCH$_2$CH$_2$); 3.6–3.7 (m, 2H, OCH$_2$); 5.2–5.8 (bs, 3H, 3 OH).

$^{13}$C-NMR (CDCl$_3$) δ(ppm): 8.8 (CH$_3$); 12.3 (arom. CH$_3$); 12.7 (arom. CH$_3$); 13.5 (arom. CH$_3$); 22.1 (CH$_2$); 25.2 (2 CH$_3$); 26.4 (CH$_2$ and CH$_3$); 34.8 (CH$_2$); 37.3 (CH$_2$); 42.0 (CH$_2$); 42.4 (qC); 73.8 (qC); 74.2 (CH$_2$); 120.2; 121.1; 128.1; 132.3; 148.7; 149.6 (6 arom. C); 183.7 (CO). IR (KBr), ν(cm$^{-1}$): 3408 (OH); 1692 (C=O). MS (m/z): 380 (M$^+$), 362, 234, 165.

EXAMPLE 14

9-Ethyl-6,6,9,13,15,16-hexamethyl-14-hydroxy-2,8-dioxabicyclo[10.4.0]hexadec-12,14,16-trien-7-one 4.65 Grams (0.021 moles) of 2,2'-dipyridyldisulfide and 5.75 g (0.022 moles) of triphenylphosphine are added to a solution containing 3.9 g (0.011 moles) of 2,2-dimethyl-5-[4-hydroxy-2-(3-hydroxy-3-methylpentyl)-3,5,6-trimethylphenoxy]pentanoic acid in 100 ml of anhydrous acetonitrile. After 3 hours at room temperature the reaction mixture is diluted with 130 ml of anhydrous p-xylene and added, by slow dripping, to a boiling solution containing 5.1 g (0.025 moles) of silver perchlorate hydrate in 340 ml of p-xylene. The reaction mixture is kept to the boiling for 18 hours, then the crude product is recovered by evaporating the solvent and purified by chromatography on column of silica gel with eluent ethyl ether-methylene chloride in 20:80 ratio. The pure product obtained by crystallization from an ethyl ether-n-hexane mixture, 1.2 g with a yield of 30%, shows the following chemical-physical characteristics:

$^1$H-NMR (CDCl$_3$ δ(ppm): 1.20–1.50 (s, 9H+m, 3H); 1.50–2.05 (m, 9H); 2.12 (s, 3H); 2.16 (s, 6H); 2.70 (m, 1H); 3.70 (m, 2H).

$^{13}$C-NMR (CDCl$_3$) δ(ppm): 12.2 (arom. CH$_3$); 13.0 (arom. CH$_3$); 25.1 (qC); 27.2 (qC); 29.8 (CH$_2$); 37.1 (CH$_2$); 42.1 (CH$_2$); 73.8 (CH$_2$O); 120.4; 132.4; 150.0 (3 arom. C); 182.0 (CO). MS (m/z): 362 (M$^+$), 165.

We claim:

1. A lactone of formula I

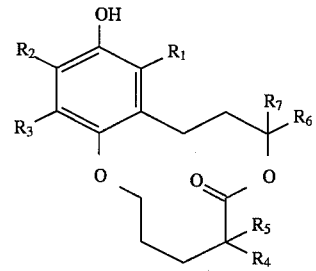

wherein R$_1$, R$_2$, R$_3$ and R$_6$ are a C$_1$–C$_3$ alkyl group and R$_4$, R$_5$ and R$_7$, independently, are a hydrogen atom or a C$_1$–C$_3$ alkyl group and a pharmacologically acceptable salt thereof, useful in the therapy of atherosclerotic and vascular pathologies.

2. The lactone according to claim 1, wherein R$_1$, R$_2$ and R$_3$ are a methyl group, R$_4$, R$_5$ and R$_7$, independently, are a hydrogen atom or a methyl group and R$_6$ is a methyl or ethyl group.

3. The lactone according to claim 1, wherein said pharmacologically acceptable salt is a member selected from the group consisting of an alanine, lysine, arginine, asparagine, glycine and trometamol salt.

4. The lactone according to claim 2, which is the 6,6,9,13,15,16-hexamethyl-14-hydroxy-2,8-dioxabicyclo[10.4.0]-hexadec-12,14,16-trien-7-one.

5. The lactone according to claim 2, which is the 9-ethyl-14-hydroxy-6,6,13,15,16-pentamethyl-2,8-dioxabicyclo[10.4.0]-hexadec-12,14,16-trien-7-one.

6. The lactone according to claim 2 which is the 14-hydroxy-9,13,15,16-tetramethyl-2,8-dioxabicyclo[10.4.0]-hexadec-12,14,16-trien-7-one.

7. The lactone according to claim 2 which is the 9-ethyl-14-hydroxy-13,15,16-trimethyl-2,8-dioxabicyclo[10.4.0]-hexadec-12,14,16-trien-7-one.

8. The lactone according to claim 2 which is the 9-ethyl-6,6,9,13,15,16-hexamethyl-14-hydroxy-2,8-dioxabicyclo[10.4.0]-hexadec-12,14,16-trien-7-one.

9. A process for the preparation of a lactone of formula I

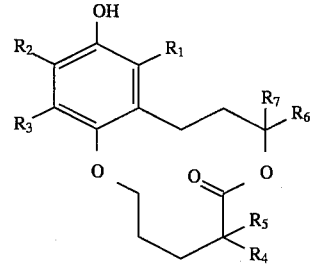

wherein R$_1$, R$_2$, R$_3$ and R$_6$ are a C$_1$–C$_3$ alkyl group and R$_4$, R$_5$ and R$_7$, independently, are a hydrogen atom or a C$_1$–C$_3$ alkyl group and a pharmacologically acceptable salt thereof, useful in the therapy of atherosclerotic and vascular pathologies which comprises the steps of a) reacting a molar equivalent of a hydroquinone of formula

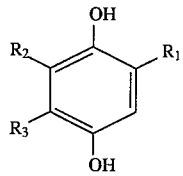

IV wherein $R_1$, $R_2$ and $R_3$ are a $C_1$–$C_3$ alkyl group with from 2 to 3 molar equivalents of an alkylvinylketone of formula

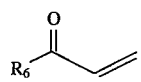

V wherein $R_6$ is a $C_1$–$C_3$ alkyl group, in presence of from 1.2 to 1.4 molar equivalents of trimethylorthoformate and at a catalytic amount of concentrated sulfuric acid, in an alcohol containing from 1 to 3 carbon atoms, under an atmosphere of inert gas and at room temperature for a period of time between 16 and 24 hours to obtain a 3,4-dihydro-2H-1-benzopyran of formula VI

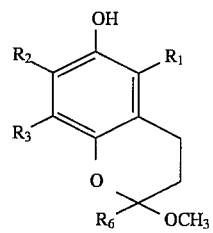

VI b) reacting a molar equivalent of said 3,4-dihydro-2H-1-benzopyran of formula VI from step a) with from 4 to 6 molar equivalents of acetic anhydride in a basic organic solvent at a temperature between 20° C. and 30° C. for a period of time between 16 and 24 hours, to obtain an ester of formula VII

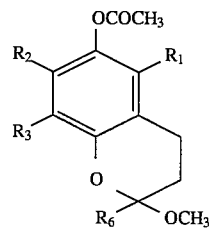

VII c) treating said ester from step b) with concentrated hydrochloric acid in an acetone-water mixture in a ratio from 1:1 to 5:1, at a temperature between 40° C. and 60° C. and for a period of time between 2 and 8 hours to selectively deprotect the hydroxyl in position 2 to obtain a compound of formula VIII

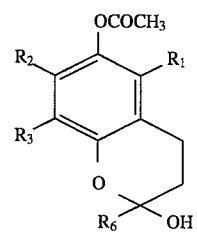

VIII d) reacting a molar equivalent of said compound of formula VIII with from 1 to 2 molar equivalents of sodium hydride and from 1 to 2 molar equivalents of an alkyl 5-bromopentanoate of formula IX

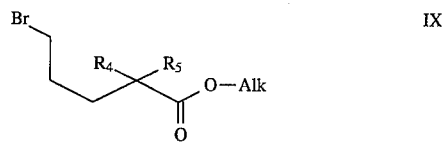

IX wherein $R_4$ and $R_5$, independently, are a hydrogen atom or a $C_1$–$C_3$ alkyl group, under an atmosphere of an inert gas and in a solvent mixture of an aromatic hydrocarbon with a polar solvent, at a temperature between 60° C. and 70° C. for a period of time between 2 and 24 hours;

whereby compound X of formula

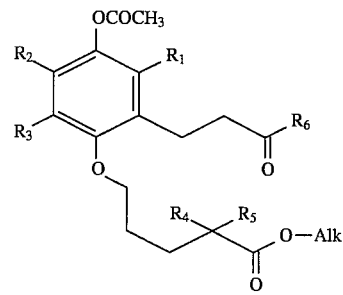

X is obtained;

e) hydrolyzing said compound X by treatment with sodium hydroxide or potassium hydroxide, in an alcohol containing from 1 to 3 carbon atoms, at a temperature between 20° C. and the boiling temperature of the reaction mixture for a period of time between 2 and 24 hours to obtain compound II of formula

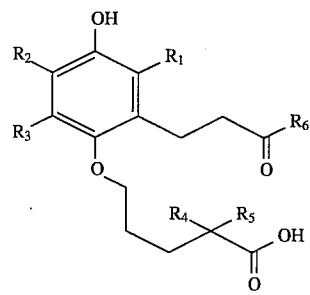

II f) reducing said compound of formula II by treatment with 2–5 molar equivalents of sodium borohydride in an alcohol containing from 1 to 3 carbon atoms, at a temperature between 25° C. and 50° C. for a period of time between 10 minutes and 6 hours to obtain a compound of formula III

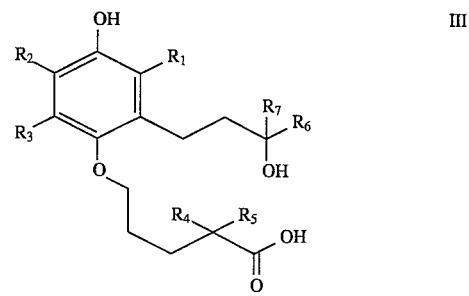

III wherein $R_7$ is hydrogen or g) preparing said compound III by reacting said compound of formula II with a Grignard reagent in an anhydrous ethereal solvent at a temperature between 20° C. and the boiling temperature of the reaction mixture for a period of time between 1 and 3 hours and then treating the reaction mixture with an aqueous solution of hydrochloric acid to obtain said compound of formula III wherein $R_7$ is a $C_1$–$C_3$ alkyl group;

h) cyclizing said compound of formula III initially in acetonitrile with from 2 to 2.2 molar equivalents of 2,2'-dipyridyldisulfide and from 2 to 2.2 molar equivalents of triphenylphosphine and subsequently with from 2 to 3 molar equivalents of silver perchlorate hydrate in an aromatic hydrocarbon, for a period of time between 12 and 24 hours at a temperature between 25° C. and the boiling temperature of the reaction mixture to obtain said lactone of formula I.

10. A compound of formula

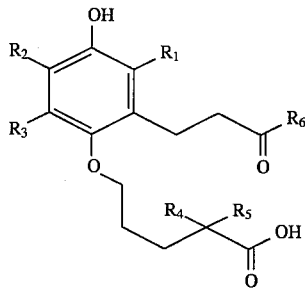

II wherein $R_1$, $R_2$, $R_3$ and $R_6$, independently, are a $C_1$–$C_3$ alkyl group and $R_4$ and $R_5$ are a hydrogen atom or a $C_1$–$C_3$ alkyl group.

11. The compound according to claim 10 which is the 2,2-dimethyl-5-[4-hydroxy-2-(3-oxobutyl)-3,5,6-trimethylphenoxy]-pentanoic acid.

12. The compound according to claim 10 which is the 2,2-dimethyl-5-[4-hydroxy-2-(3-oxopentyl)-3,5,6-trimethylphenoxy]pentanoic acid.

13. The compound according to claim 10 which is the 5-[4-hydroxy-2-(3-oxobutyl)-3,5,6-trimethylphenoxy]pentanoic acid.

14. The compound according to claim 10 which is the 5-[4-hydroxy-2-(3-oxopentyl)-3,56-trimethylphenoxy]pentanoic acid.

15. A compound of formula

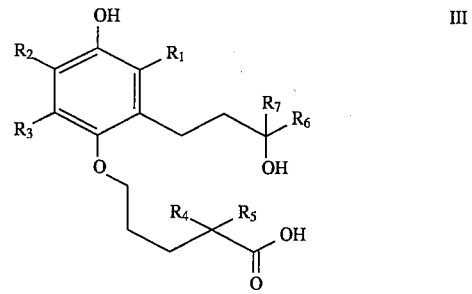

III wherein $R_1$, $R_2$, $R_3$ and $R_6$, independently, are a $C_1$–$C_3$ alkyl group and $R_4$, $R_5$ and $R_7$ are a hydrogen atom or a $C_1$–$C_3$ alkyl group.

16. The compound according to claim 15 which is the 2,2-dimethyl-5-[4-hydroxy-2-(3-hydroxybutyl)-3,5,6-trimethylphenoxy]-pentanoic acid.

17. The compound according to claim 15 which is the 2,2-dimethyl-5-[4-hydroxy-2-(3-hydroxypentyl)-3,5,6-trimethylphenoxy]pentanoic acid.

18. The compound according to claim 15 which is the 5-[4-hydroxy-2-(3-hydroxybutyl)-3,5,6-trimethylphenoxy] pentanoic acid.

19. The compound according to claim 15 which is the 5-[4-hydroxy-2-(3-hydroxypentyl)-3,5,6-trimethylphenoxy] pentanoic acid.

20. The compound according to claim 15 which is the 2,2-dimethyl-5-[4-hydroxy-2-(3-hydroxy-3-methylpentyl)-3,5,6-trimethylphenoxy]pentanoic acid.

* * * * *